United States Patent [19]
Amberg et al.

[11] Patent Number: 5,864,012
[45] Date of Patent: Jan. 26, 1999

[54] ACTIVE PEPTIDE AND ITS PREPARATION

[75] Inventors: Wilhelm Amberg, Friedrichsdorf; Harald Bernard, Bad Dürkheim; Ernst Buschmann, Ludwigshafen, all of Germany; Andreas Haupt, Westboro, Mass.; Lothar Janitschke, Kleinniedesheim, Germany; Bernd Janssen; Ulrich Karl, both of Ludwigshafen, Germany; Andreas Kling, Mannheim, Germany; Stefan Müller, Speyer, Germany; Bernd de Potzolli, Bad Dürkheim, Germany; Kurt Ritter, Heidelberg, Germany; Marco Thyes, Ludwigshafen, Germany; Thomas Zierke, Böhl-Iggelheim, Germany

[73] Assignee: BASF Aktiengesellschaft, Ludwigshafen, Germany

[21] Appl. No.: 732,453

[22] PCT Filed: Apr. 26, 1995

[86] PCT No.: PCT/EP95/01577

§ 371 Date: Nov. 4, 1996

§ 102(e) Date: Nov. 4, 1996

[87] PCT Pub. No.: WO95/30691

PCT Pub. Date: Nov. 16, 1995

[30] Foreign Application Priority Data

May 6, 1994 [DE] Germany ............ 44 15 997.8

[51] Int. Cl.⁶ ........................................ C07K 7/00
[52] U.S. Cl. ................. 530/330; 530/333; 530/338; 530/343
[58] Field of Search .................. 530/330, 333, 530/338, 343

[56] References Cited

FOREIGN PATENT DOCUMENTS

93/23424  11/1993  WIPO.

OTHER PUBLICATIONS

Pettit et al., *J. Am. Chem. Soc.*, 113(17), 6692–3. (abstract), 1991.
Pettit et al., *Tetrahedron*, 50(42), 12097–12108, 1994.
Gross et al., "The Peptides: Analysis, Synthesis, Biology", vol. 4, 1981, preface p. xi.
Ullmann's Enc. of Ind. Chem., vol. A19, p. 168, (1991).

*Primary Examiner*—Cecilia J. Tsang
*Assistant Examiner*—C. Delacroix-Muirheid
*Attorney, Agent, or Firm*—Keil & Weinkauf

[57] ABSTRACT

The compound $Me_2Val$—Val—MeVal—Pro—Pro—NHBzl·HCl is described. It is prepared from Z—Val—Val—MeVal—Pro—$OR^1$ where Z and $R^1$ have the meanings stated in the description. The compound shows antineoplastic activity.

5 Claims, No Drawings

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
       ( A ) LENGTH: 5 amino acids
       ( B ) TYPE: amino acid
       ( D ) TOPOLOGY: linear ( x i ) SEQUENCE DESCRIPTION: SEQ ID NO: 1:

Xaa  Val  Xaa  Pro  Pro
 1                    5

( 2 ) INFORMATION FOR SEQ ID NO: 2:

( i ) SEQUENCE CHARACTERISTICS:
       ( A ) LENGTH: 5 amino acids
       ( B ) TYPE: amino acid
       ( D ) TOPOLOGY: linear ( x i ) SEQUENCE DESCRIPTION: SEQ ID NO: 2:

Val  Val  Xaa  Pro  Pro
 1                    5

ACTIVE PEPTIDE AND ITS PREPARATION

The invention relates to a novel active peptide and to its preparation and suitable starting materials therefor.

The PCT Application WO 93/23424 describes peptide-based active substances which have interesting antineoplastic activities. A particularly good effect is shown by the pentapeptide of Example 234 in the said application, which has the following formula:

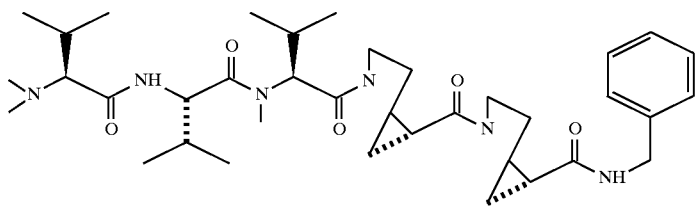

Me$_2$Val—Val—MeVal—Pro—Pro—NHBzl SEQ ID NO: 1

Me$_2$Val is N,N-dimethyl-L-valine, MeVal is N-methyl-L-valine and Bzl is benzyl.

The peptide can, according to the said PCT application, be prepared by a solid-phase method starting from proline. This gives a poor yield of impure active substance. Elaborate chromatographic purification is necessary. The solid-phase method is, moreover, suitable only for preparing small amounts of substance. It has not to date proven possible to prepare the substance of Example 234 of WO 93/23424 in crystalline form. The active substance is in the form of a resin. This makes it difficult to remove residual solvent completely. Costly purification steps (spray drying, freeze drying) are necessary. Pharmaceutical processing of the substance is impeded. Larger amounts of substance are necessary for testing and launching it. A process which can be implemented industrially is needed to prepare the active substance in crystalline form if possible.

We have now found a process which affords the active substance without racemization in high purity so that the substance can be converted without difficulty into a crystalline salt, the hydrochloride.

The invention relates to a process for preparing Me$_2$Val—Val—MeVal—Pro—Pro—NHBzl·HCl, which comprises in a compound of the formula II Z—Val—Val—MeVal—Pro—OR$^1$    II where
R$^1$ is C$_{1-5}$-alkyl and
Z is a benzyloxycarbonyl protective group which may be substituted on the phenyl ring, A a) eliminating the protective group Z on the N terminus, and in the resulting compound
1) dimethylating the free amino group on the N terminus,
2) hydrolyzing the alkoxy group —OR$^1$ on the C terminus and b) coupling the resulting compound of the formula Me$_2$Val—Val—MeVal—Pro—OH    V with proline benzylamide XII
or
B a) removing the alkoxy group —OR$^1$ on the C terminus and
b) coupling the resulting compound of the formula Z—Val—Val—MeVal—Pro—OH    IX with proline benzylamide XII, and in the resulting compound of the formula Z—Val—Val—MeVal—Pro—Pro—NHBzl    XI SEQ ID NO: 2

1) removing the protective group Z on the N terminus and
2) dimethylating the free amino group on the N terminus and converting the resulting compound into its hydrochloride.

Process A takes place in accordance with the following reaction cheme:

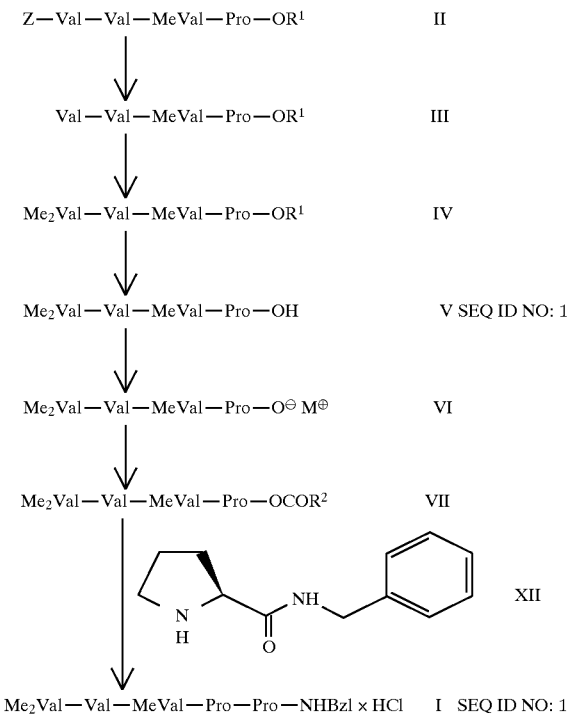

The meanings of the substituents in the above scheme as elsewhere in the description are as follows:

R$^1$: C$_{1-5}$-alkyl such as methyl, ethyl, n-propyl, isopropyl, n-butyl, tert-butyl, isobutyl, pentyl and preferably methyl and ethyl, R$^2$: tert-butyl, 2-ethylhexyl, C$_{1-4}$-alkoxy such as methoxy, ethoxy, isobutoxy, Z: benzyloxycarbonyl, which is unsubstituted or substituted on the phenyl ring by halogen, C$_{1-4}$-alkyl, C$_{1-4}$-alkoxy, C$_{1-4}$-acyloxy or nitro and in particular by 2-Cl, 3-Cl, 4-Cl, 4-Br, 4-CH$_3$O—, 4-CH$_3$COO—, 2-NO$_2$ and 4-NO$_2$ M$^⊕$; K$^⊕$, Na$^⊕$, Li$^⊕$ or an ammonium ion such as $^⊕$NH(C$_2$H$_5$)$_3$ Bzl:benzyl
Me: methyl.

The tetrapeptide ester II is dissolved in a suitable solvent, eg. an alcohol such as methanol, ethanol, isopropanol, butanol, an ether such as THF, dioxane, MTBE, an ester such as ethyl acetate, or glacial acetic acid. After addition of a suitable catalyst, eg. Pd/C or Pt/C, hydrogen is passed in at from 0° to 50° C., preferably from 10° to 30° C. Introduction of hydrogen can take place under atmospheric pressure or up to 10 bar. The reaction rate can be increased by allowing a certain amount of gas to escape. After hydrogen uptake is complete, 2–5 equivalents of formaldehyde are added in the form of an aqueous solution, of the gas or of paraformaldehyde. Subsequently hydrogen is passed in further under the conditions described above. The catalyst is then filtered off. IV can be purified by crystallization as hydrochloride from a suitable solvent or mixture of solvents, isopropanol/methyl tert-butyl ether having proven suitable. Traces of the Z-tetra-peptide ester II in IV can be removed by extraction methods.

The ester IV is hydrolyzed in a suitable solvent, eg. an alcohol such as methanol, ethanol, isopropanol, an ether such as MTBE, THF, dioxane, a hydrocarbon such as toluene, xylene, or a chlorinated hydrocarbon such as 1,2-dichloroethane, methylene chloride, chloroform, with and without addition of water and with a suitable base such as NaOH, KOH, LiOH. The ester cleavage can also be carried out by acids. Particularly suitable when $R^1$=tert-butyl are $CF_3CO_2H$ and a solution of HCl in dioxane.

The resulting tetrapeptide acid V must subsequently be coupled with proline benzylamide XII to give the pentapeptide I. Racemization readily takes place in such coupling reactions. G. Pettit et al. (J. Am. Chem. Soc. 113, 6692–3 (1991)) therefore use DEPC [(OEt)$_2$POCN] as coupling reagent for an analogous coupling with the tetrapeptide acid V. DEPC cannot be bought in large amounts. The method therefore requires additional process steps with poisonous phosphorus and cyanide reagents.

Cyanide-containing wastes cause disposal problems. The process is therefore unsuitable for industrial implementation. A peptide coupling method which can be carried out particularly straightforwardly on the industrial scale is the mixed anhydride method (see, for example, J. Meienhofer in The Peptides, Analysis, Synthesis, Biology, Volume 1, Academic Press, Orlando, 1979, pages 264–314). This entails the acid V being deprotonated with a suitable base, eg. a tertiary amine such as triethylamine, N-methylmorpholine, dicyclohexylethylamine, diisopropylethylamine, to VI. The esters of the formula IV can also be converted directly into the salts VI with bases such as NaOH, KOH, LiOH. The compounds VI are reacted with an acid chloride $ClCOR^2$ to give the mixed anhydride of the formula VII. Besides pivaloyl chloride it is also possible to use other acid chlorides such as 2-ethylhexanoyl chloride, ethyl chloroformate, methyl chloroformate and isobutyl chloroformate. The mixed anhydrides are very prone to racemization (see, for example, J. Meienhofer in The Peptides, Volume 1, Academic Press, Orlando, 1979, pages 276 et seq.).

Surprisingly, it was then possible to react the tripeptide acid V by the mixed anhydride method completely without racemization. Particularly good results were obtained with the mixed anhydride prepared from V and pivaloyl chloride. In contrast to recently published results (N. L. Benoiton et al., Can. J. Chem. 65, 619–625 (1987)), reaction with pivaloyl chloride gives better results, in terms of selectivity and yield, than reaction with chloroformic esters. Preparation of the mixed anhydride VII and the subsequent coupling of proline benzylamide are carried out at from −20° to −5° in a suitable solvent such as dioxane, NMP, THF, toluene, methylene chloride, dimethylformamide. In place of proline benzylamide XII it is also possible to use a suitable salt of this compound, eg. the bisulfate, the methylsulfonate, the hydrochloride or the hydrobromide. In this case it is necessary to add another equivalent of base, eg. triethylamine. After the peptide coupling and conventional workup by extraction, the crude product is dissolved in a suitable solvent, eg. a hydrocarbon such as toluene, xylene, or an ether such as diethyl ether, THF, dioxane, methyl tert-butyl ether, a ketone such as acetone, methyl ethyl ketone, diethyl ketone, cyclohexanone, or chlorinated solvents such as methylene chloride, chloroform, 1,2-dich-loroethane. The hydrochloride I is precipitated by introducing gaseous HCl or metering in a solution of HCl in a suitable solvent, eg. THF, methanol, isopropanol, n-pentanol, diisopropyl ether. A particularly suitable process has proven to be one in which the free base of the pentapeptide is initially dissolved in methyl ethyl ketone, and subsequently a solution of HCl in isopropanol is added.

Process B takes place in accordance with the following scheme:

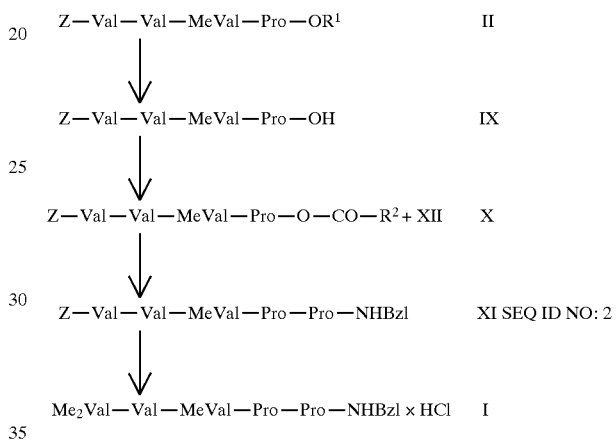

The hydrolysis of the ester II, the preparation of the mixed anhydrides X and the peptide coupling to give XI take place as for the sequence IV→V→VI→VII→I. Elimination of the Z protective group and dimethylation to give I take place as for the conversion II→III→IV.

The mixed anhydride method also, surprisingly, takes place without racemization in variant B. In contrast to the results published by Benoiton, the best yields are obtained with the mixed anhydride prepared from the acid IX and pivaloyl chloride.

The starting material II needed to prepare the peptide I can be prepared from Z—Val—O—CO—R$^2$ (XIII) and Val—MeVal—Pro—OR$^1$ (XIV).

The novel process provides active substance I in crystalline form. The peptide can be further purified in a simple way by recrystallization. Elaborate chromatographic purification steps are unnecessary.

The invention also relates to the following precursors for preparing I:

| | |
|---|---|
| Z—Val—Val—MeVal—Pro—OR$^1$ | II |
| Val—Val—MeVal—Pro—OR$^1$ | III |
| Me$_2$Val—Val—MeVal—Pro—O—CO—R$^2$ | VII |
| Z—Val—Val—MeVal—Pro—OH | IX |
| Z—Val—Val—MeVal—Pro—O—CO—R$^2$ | X |
| Z—Val—Val—MeVal—Pro—Pro—NHBzl | XI SEQ. ID NO:2 | where R$^1$ and Z have the meanings stated in claim 3, and R$^2$ is tert-butyl, 2-ethylhexyl, C$_{1-4}$-alkoxy, methoxy, ethoxy and isobutoxy.

The compound I has activity on solid tumors (tumors of the lungs, the breast, the intestine, the bladder, the rectum, the uterus, the prostate) on leukemia, lymphomas and other neoplastic disorders.

The following examples illustrate the invention.

EXAMPLE 1 (Process A)

A. Preparation of the Starting Materials
a. Z—Val—Val—MeVal—Pro—OMe (II, $R^1$=Me)

39.6 kg (83.3 mol) of Z—Val—MeVal—Pro—OMe (VIII) in 320 l of methanol were introduced together with 4 kg of 5% palladium/carbon into a 400 l hydrogenation vessel. Then, while cooling at 20–30° C., hydrogen was passed in until precursor was no longer detectable in the reaction solution. The catalyst was filtered off as the contents of the vessel were discharged. The filtrate was worked up by concentration to 50 l in a 400 l enameled vessel under waterpump vacuum. Subsequently 50 of toluene were run in and the mixture was extracted with 40 l of 2N HCl. The toluene phase was extracted once more with 40 l of 1N hydrochloric acid and then discharged. The collected acidic aqueous phase was returned to the vessel and, after addition of 40 l of methylene chloride, adjusted to pH 9 by running in 50% strength sodium hydroxide solution while stirring vigorously and cooling. After phase separation, the methylene chloride phase was discharged and the aqueous phase was extracted twice more with 40 l of methylene chloride each time. The collected methylene chloride solution of the product is washed with water until neutral. The methylene chloride phase is subsequently concentrated to 90 l to afford Val—MeVal—Pro—OMe (XIV, $R^1$=$CH_3$).

Yield: 24.2 kg=85.2%

17.84 kg (70.88 mol) of Z-valine and 4.59 kg (74.42 mol) of triethylamine are dissolved in 170 l of methylene chloride in a 400 l vessel. 8.58 kg (70.88 mol) of pivaloyl chloride are metered into this solution at −5° to −10° C. After a reaction time of 2 h at −5° C., a solution of 24.2 kg of Val—MeVal—Pro—OMe in 86 l of methylene chloride was run in at −5° C. After a further 2 h at −5° C., the mixture was heated to 20° C. and stirred at this temperature for 12 h. For workup, 50 l of water were added and, after removal of the aqueous phase, the organic phase was extracted once with 40 l of 2N hydrochloric acid and twice with 40 l of 2N sodium hydroxide solution each time. After the organic phase has been washed with water to neutrality, the methylene chloride solvent was removed by distillation and replaced by 300 l of diisopropyl ether. The product was crystallized by heating the emulsion of the oily product to 60° C., adding seed crystals and keeping at 60° C. for 7 h. The crystallization was completed by stirring successively at 50° C. for 5 h and at 40° C. for 5 h and then cooling to 20° C. The crystals were filtered off through a 120 l pressure filter and dried in a stream of nitrogen.

Yield: 32.2 kg=79%

Melting point: 134–135° C.

b. Proline benzylamide hydrochloride (XII×HCl)

48.2 g of pivaloyl chloride were added dropwise to a solution of 99.7 g of Z-proline and 58 ml of triethylamine in 1 l of $CH_2Cl_2$ at −10° to −15° C. The mixture was stirred at −10° C. for 45 min and then, over the course of 0.5 h, 42.8 g of benzylamine in 500 ml of $CH_2Cl_2$ were added at −10° C. The mixture was then stirred at room temperature for 1 h. The $CH_2Cl_2$ solution was subsequently washed twice with 500 ml of water, twice with 500 ml of 10% strength aqueous $NaHCO_3$ solution, twice with 500 ml of water, twice with 500 ml of 5% strength aqueous citric acid solution and twice with 500 ml of water, dried over $Na_2SO_4$ and evaporated. The 120 g of residue were taken up in 200 ml of ethyl acetate. 1.2 l of n-heptane were added to the solution, the mixture was stirred for one hour, and the product was filtered off with suction and dried at 50° C. under reduced pressure.

Yield: 110 g, 81.3%

Melting point: 93°–94° C.

110 g of the Z-proline benzylamide obtained in this way were dissolved in 1.5 l of methanol. After addition of 0.5 g of Pd/C (10%) hydrogen was passed in. The solution took up 0.5 l of $H_2$ over the course of 1.5 h at room temperature. After removal of the catalyst by filtration and evaporation, 4.6 g of a yellow oil remained.

413 g of the proline benzylamide obtained in this way were dissolved in 400 ml of isopropanol. 630 ml of a saturated solution of HCl in isopropanol were added, the resulting suspension was stirred at 0°–5° C. for 2 h, and the solid was filtered off with suction and washed twice with 250 ml of isopropanol. The residue was dried at 50° C. under reduced pressure to obtain 401 g of proline benzylamide hydrochloride; $a_D^{20}$:—45°

B. Preparation of the final product
a. 1
$Me_2$Val—Val—MeVal—Pro—OMe×HCl (IV×HCl, $R^1$=Me)

20 kg (34.8 mol) of Z—Val-Val—MeVal—Pro—OMe (II, $R^1$=Me) were introduced together with 2 kg of 5% palladium/carbon into 200 l of methanol in a 400 l hydrogenation vessel. Then, while cooling, hydrogen was passed in at 20° C. until precursor was no longer detectable in the reaction solution. Subsequently 8.46 kg of 37% strength (104 mol) aqueous formaldehyde solution were added, and hydrogenation was continued at 20° C. until hydrogen uptake ceased. The catalyst was filtered off as the contents of the vessel were discharged. The filtrate was worked up by concentrating to 50 l in a 400 ml enameled vessel under waterpump vacuum. Then 200 l of isopropanol were added, and the mixture was again concentrated to 50 l. The residue was then dissolved in 135 l of methyl tert-butyl ether, and one equivalent of isopropanolic HCl was added while cooling at 20° C. The resulting suspension was stirred further at 20° C. for 3–4 h and at 0–5° C. for 2 h and then filtered through a 120 l pressure filter. The filter cake was washed once with 50 l of fresh methyl tert-butyl ether.

Yield: 16.2 kg =92.3%

Melting point: 224° C. (decomposition)

a.2

It was also possible to isolate the intermediates Val—Val—MeVal—Pro—OMe (III, $R^1$=$CH_3$) when workup was carried out as follows after the first hydrogenation stage:

The reaction solution was separated from the catalyst and concentrated. The residue was taken up in ethyl acetate. The ethyl acetate solution was extracted twice with 2N hydrochloric acid. The acidic aqueous phase was adjusted to pH 9 with sodium hydroxide solution and extracted twice with methylene chloride. The methylene chloride phase was then washed until neutral and evaporated.

HPLC 96,8%

$^1$H-NMR (400 MHz, $CDCl_3$ / $TMS_{inst.}$):

δ(ppm): 0.84–1.08 (m, 18H); 1.45–1.6 (S, broad, $NH_2$); 1.85–2.15 (m, 4H); 2.18–2.38 (m, 3H);

3.15 (s, N—$CH_3$); 3.25 (d, 1H); 3.65–3.75 (m, 1H);

3.73 (s, O—$CH_3$); 3.9–4.05 (m, 1H); 4.38–4.45 (m, 1H);

4.73–4.83 (m, 1H); 5.12 (d, 1H); 7.9 (d, NH)

a.3

$Me_2$Val—Val—MeVal—Pro—OMe×HCl (IV×HCl, $R^1$=Me) can also be prepared by the following method which dispenses with isolation and purification of the intermediate Z—Val—Val—MeVal—Pro—OMe (II, $R^1$=Me):

128 g (0.51 mol) of Z-valine and 55.1 g (0.54 mol) of triethylamine were dissolved in 1.2 l of methylene chloride in a 4 l flask. 62.1 g (0.51 mol) of pivaloyl chloride were added to this solution at −5° C. to −10° C. After a reaction time of 2 h at −5° C., a solution of 174.6 g (0.51 mol) of Val—MeVal—Pro—OMe in 0,8 l of methylene chloride was run in, and the mixture was stirred at −5° C. for a further 2 h and then, after warming to 20° C., for a further 12 h. 370 ml of water were then added to the mixture. After phase separation, the methylene chloride phase was washed once with 290 ml of 2N hydrochloric acid, twice with 290 ml of 2N sodium hydroxide solution each time and three times with 370 ml of water. The methylene chloride solvent was subsequently evaporated off and replaced by 3 l of methanol. To this solution was added a suspension of 30 g of 5% palladium/carbon in 110 ml of water and hydrogenation was carried out at 25° C. using a gas-introduction stirrer and hydrogen burette until one equivalent of hydrogen had been taken up. Then 123 g (1.53 mol) of 37% strength aqueous formaldehyde solution were added and hydrogenation was continued until a further 2 equivalents of hydrogen had been taken up. The catalyst was then removed and the solution was evaporated in a rotary evaporator. The remaining oil was dissolved in 670 ml of isopropanol and 2.6 l of methyl tert-butyl ether. One equivalent of isopropanolic HCl was added to this solution. The resulting suspension was stirred at 20° C. for a further 12 h and then filtered with suction. The filter cake was washed with a little methyl tert-butyl ether and subsequently dried at 40° C. in a vacuum oven.

Yield: 182.8 g=71%
Melting point: 224° C. (decomposition)

b. Me$_2$Val—Val—MeVal—Pro—Pro—NHBzl×HCl (I)

15.9 kg (31.5 mol) of Me$_2$Val—Val—MeVal—Pro—OMe×HCl (IV×HCl, R$^1$=CH$_3$) were introduced together with 140 l of toluene and 15 l of methanol into a 400 l vessel. To this were added 3.15 kg (76.38 mol) of sodium hydroxide pellets. After hydrolysis was complete, ie. after 3 h at 20° C., the mixture was neutralized by adding isopropanolic HCl. It was subsequently azeotropically distilled with toluene under 100 mbar until free of alcohol and water. The solvent which was distilled off was successively replaced by toluene. Subsequently, 80 l of methylene chloride and 6.44 kg (63.0 mol) of triethylamine (99% pure) were added, the mixture was cooled to −5° C. and, at this temperature, 3.84 kg (31.5 mol) of pivaloyl chloride were metered in. After reaction for 2 hours, 7.6 kg (31.5 mol) of Pro-NHBzl×HCl were added a little at a time at −5° C. to 0° C. After the mixture had stood at −5° C. for 2 h it was warmed to 20° C. and left to react for a further 6 h. Subsequently the added methylene chloride was removed by distillation under 500 mbar, and 80 l of toluene were added. Then 50 l of water were added and the pH of the aqueous phase was adjusted to pH 9. After vigorous stirring, the aqueous phase was separated off, and the organic phase was washed once with 25 l of water. The organic phase was subsequently extracted twice with 50 l of 2N hydrochloric acid each time. The product was back-extracted from the acidic aqueous phase after adjustment of the pH to 9 by extraction 3 times with 50 l of methylene chloride each time. After the methylene chloride phase had been washed with water to neutrality, the methylene chloride was removed and replaced by 180 l of methyl ethyl ketone. The solution was warmed to 40° C. and one equivalent (31.5 mol) of isopropanolic HCl was added. The resulting suspension was warmed to 60° C. and subsequently stirred for 12 h without further input of heat. It was then cooled to 20° C. and stirred for a further 5 h. It was subsequently cooled to 5° C. and filtered through a 120 l pressure filter. The filter cake was washed with 60 l of fresh methyl ethyl ketone at 5° C. After initial drying on the filter, the product is dried to constant weight in a vacuum oven at 40° C.

Yield: 14.36 kg=67%
Melting point: 214° C. (decomposition)

EXAMPLE 2 (Process B)

a. Z—Val—Val—MeVal—Pro—OH (IX)

117 g (0.2 mol) of Z—Val—Val—MeVal—Pro—OMe (II, R$^1$=Me, Example 1Aa) are dissolved in 900 ml of methanol and 47.5 ml of water in a 2 l flask. Subsequently 18 g (0.45 mol) of sodium hydroxide pellets were added, and the mixture was stirred at 20° C. for 12 h. For workup, 250 ml of water were added and the methanol was distilled off. Then sufficient ethyl acetate was added to produce clear phase separation (about 500 ml). The ethyl acetate phase was separated off. The aqueous phase was acidified to pH 1 with hydrochloric acid and extracted twice with 500 ml of methylene chloride. The organic phase was then evaporated to dryness.

Yield: 105 g=96.4%
$^1$H-NMR (200 MHz, CDC$_3$/TMS$_{int.}$)
δ(ppm): 0.6–1.2 (m, 18H); 1.7–2.45 (m, 7H); 3.2 (s, N—CH$_3$);
3.55–3.95 (m, 2H); 4.05–4.2 (m, 1H); 4.35–4.5 (m, 1H); 4.68–4.85 (m, 1H); 4.98–5.2 (m, 3H); 5.93 (d, Val-1NH); 7.2–7.4 (m, 5H); 7.53–7.68 (Val-2NH); 9.6–10.2 (s, broad, COOH)

b. Z—Val—Val—MeVal—Pro—Pro—NHBzl (XI) SEQ ID NO: 2

5 g of Z—Val—Val—MeVal—Pro—OH (8.75 mmol) (IX) were dissolved in 50 ml of CH$_2$Cl$_2$, 1.79 g (17.5 mmol) of triethylamine were added dropwise, the mixture was cooled to 10° C. and, at this temperature, 1.08 g (8.75 mmol) of pivaloyl chloride were added dropwise. After stirring at 10° C. for 2 h, a solution of 2.11 g (8.75 mmol) of Pro-NHBzl×HCl in 10 ml of methanol was added dropwise at this temperature, and the mixture was stirred at 10° C. for 2 h and at room temperature overnight.

The reaction mixture was washed 3 times with 50 ml of water each time, once with 50 ml of water at pH 9 and twice more with 50 ml of water each time. The methylene chloride solution was evaporated in a rotary evaporator to leave 5.3 g (81.4%) of white crystalline product (purity: 88.7%).

Melting point: 118–122° C.

c. Me$_2$Val—Val—MeVal—Pro—Pro—NHBzl×HCl SEQ. ID NO: 1

12 g of Z—Val—Val—MeVal—Pro—Pro—NHBzl (XI) SEQ ID. NO: 2 were dissolved in 200 ml of methanol. To this were added 2 g of 5% palladium/carbon (suspended in 20 ml of water) and hydrogenation was carried out at 20° C. until hydrogen uptake ceased. Subsequently, 6.5 g of 37% strength aqueous formaldehyde solution were added, and hydrogenation was continued until hydrogen uptake ceased. The catalyst was then separated off and the reaction solution was evaporated. The residue was taken up in toluene and concentrated again, and a further 200 ml of toluene were added and the mixture was filtered. The toluene solution was subsequently extracted 2× with 50 ml of 2N hydrochloric acid. The acidic aqueous phase was adjusted to pH 9 with sodium hydroxide solution and extracted three times with 50 ml of methylene chloride. The methylene chloride phase was washed with water until neutral and concentrated. The crude base was taken up in a solution of 150 ml of methyl ethyl ketone and 7.5 ml of isopropanol. The product salt was precipitated from this solution by adding 4 g of 25% strength isopropanolic HCl at 40° C. The suspension is stirred at 20° C. for 3 h and at 0°–5° C. for one hour and then filtered with suction.

Yield: 7.1 g
Purity: 99.1% (HPLC percent area)
Melting point: 214° C. (decomposition)

b) coupling the resulting compound of the formula

Z—Val—Val—MeVal—Pro—OH    IX with proline benzylamide, and in the resulting compound of the formula Z—Val—Val—MeVal—Pro—Pro—NHBzl    XI SEQ ID NO: 2

1) removing the protective group Z on the N terminus and
2) dimethylating the free amino group on the N terminus and converting the resulting compound into its hydrochloride.

We claim:

1. A process for preparing Me$_2$Val—Val—MeVal—Pro—Pro—NHBzl·HCl, which comprises in a compound of the formula II Z—Val—Val—MeVal—Pro—OR$^1$    II where
   R$^1$ is C$_{1-5}$-alkyl and
   Z is a benzyloxycarbonyl protective group which may be substituted on the phenyl ring,
A a) eliminating the protective group Z on the N terminus, and in the resulting compound
   1) dimethylating the free amino group on the N terminus,
   2) hydrolyzing the alkoxy group —OR$^1$ on the C terminus and
   b) coupling the resulting compound of the formula Me$_2$Val—Val—MeVal—Pro—OH    V with proline benzylamide
or
B a) removing the alkoxy group —OR$^1$ on the C terminus and 2. A process as claimed in claim 1, wherein the tetrapeptidecarboxylic acids of the formulae V and IX are initially, for the purpose of coupling with proline benzylamide, converted into mixed anhydrides with pivalic acid.

3. The compound Me$_2$Val—Val—MeVal—Pro—O—CO—R$^2$ where R$^2$ is tert-butyl, 2-ethylhexyl, C$_{1-4}$-alkoxy, methoxy, ethoxy or isobutoxy.

4. A compound selected from the group consisting of

| | |
|---|---|
| Z—Val—Val—MeVal—Pro—OR$^1$ | II; |
| Val—Val—MeVal—Pro—OR$^1$ | III; |
| Z—Val—Val—MeVal—Pro—OH | IX; |
| Z—Val—Val—MeVal—Pro—O—CO—R$^2$ | X; |
| Z—Val—Val—MeVal—Pro—Pro—NHB$_z$l | XI (SEQ. ID NO:2); | where R$^1$ is C$_{1-5}$-alkyl;
R$^2$ is a member selected from the group consisting of tert-butyl, 2-ethylhexyl, C$_{1-4}$-alkoxy, methoxy, ethoxy and isobutoxy; and
Z is a benzyloxycarbonyl protective group which may be substituted on the phenyl ring.

5. The compound Me$_2$Val—Val—MeVal—Pro—Pro—NHBzl. HCl (SEQ ID NO: 1 in crystalline form.

* * * * *